US 6,683,965 B1

(12) United States Patent
Sapiejewski

(10) Patent No.: US 6,683,965 B1
(45) Date of Patent: Jan. 27, 2004

(54) IN-THE-EAR NOISE REDUCTION HEADPHONES

(75) Inventor: Roman Sapiejewski, Boston, MA (US)

(73) Assignee: Bose Corporation, Framingham, MA (US)

( * ) Notice: Subject to any disclaimer, the term of this patent is extended or adjusted under 35 U.S.C. 154(b) by 1592 days.

(21) Appl. No.: 08/546,050

(22) Filed: Oct. 20, 1995

(51) Int. Cl.[7] ............................................. H04R 25/00
(52) U.S. Cl. ........................ 381/380; 381/370; 381/371; 381/382
(58) Field of Search ............................ 381/25, 68, 68.6, 381/71, 72, 74, 94, 183, 187, 309, 322, 327, 328, 71.6, 380, 382, 370, 94.1; 181/129, 135; 73/585

(56) References Cited

U.S. PATENT DOCUMENTS

| | | | |
|---|---|---|---|
| 3,448,224 A | * | 6/1969 | Giller .......................... 381/68.6 |
| 3,647,969 A | | 3/1972 | Korn |
| 3,890,474 A | | 6/1975 | Glicksberg |
| 4,055,233 A | | 10/1977 | Huntress ...................... 181/135 |
| 4,089,332 A | | 5/1978 | Rose ............................ 128/152 |
| 4,395,588 A | | 7/1983 | Franssen et al. |
| 4,455,675 A | | 6/1984 | Bose et al. ..................... 381/74 |
| 4,622,440 A | | 11/1986 | Slavin ......................... 381/68.1 |
| 4,677,676 A | | 6/1987 | Eriksson ....................... 381/71 |
| 4,870,688 A | | 9/1989 | Voroba et al. .................. 381/68 |
| 4,985,925 A | | 1/1991 | Langberg et al. ............... 381/72 |
| 5,134,655 A | * | 7/1992 | Jenssen ....................... 381/183 |
| 5,208,868 A | * | 5/1993 | Sapiejewski .................. 381/74 |
| 5,305,387 A | | 4/1994 | Sapiejewski .................. 381/71 |

FOREIGN PATENT DOCUMENTS

| | | | | |
|---|---|---|---|---|
| DE | 3210034 | * | 9/1982 | .................. 381/187 |
| FR | 2604551 | | 4/1986 | |
| GB | 2172769 | | 9/1986 | |

\* cited by examiner

Primary Examiner—Huyen Le
(74) Attorney, Agent, or Firm—Fish & Richardson P.C.

(57) ABSTRACT

An in-the-ear earphone which is placed on a user's ear including a cushion and a shell body defining an internal cavity. The shell body has an extended portion shaped and sized to fit into a concha of the user's ear. The extended portion includes an aperture at an end thereof which aligns with the user's ear when the earphone is being worn by the user. The extended portion defines a passageway extending from the aperture to the internal cavity. The cushion covers at least part of the extended portion of the shell body and has an opening aligned with the aperture.

45 Claims, 5 Drawing Sheets

IN-THE-EAR NOISE REDUCTION HEADPHONES

CROSS REFERENCE TO RELATED APPLICATIONS

The following patent application is related to the present application: U.S. Ser. No. 08/261,802 filed Jun. 17, 1994, incorporated herein by reference. Also as background, reference is made to U.S. Pat. No. 5,305,387, issued Apr. 19, 1994 also incorporated herein by reference.

BACKGROUND OF THE INVENTION

The invention generally relates to earphones, in particular, in-the-ear earphones, designed to provide noise attenuation.

There are at least three headphone design types, which are generally categorized in terms of how they are worn by the user. The three design types are referred to as around-the-ear, on-the-ear, and in-the-ear headphones. Around-the-ear headphones have large earphones that resemble earmuffs. Like earmuffs, the around-the-ear earphone covers and surrounds the ear. It typically provides very good noise attenuation but it is not particularly comfortable, especially for people using eyeglasses. Since the earphone surrounds the user's ear, it cuts off air circulation behind the ear and thus can be uncomfortably warm in hot weather.

In addition, under some circumstances such as when intelligibility of local conversation is important, the high level of passive attenuation provided at high frequencies by the around-the-ear headphones will cause intelligibility of external stimuli to suffer. There are many environments or applications in which it is desirable to hear external conversation or sound, for example, in certain industrial applications and in airplanes. In large industrial plants where a lot of machine noise is present, it may be useful to use radios as a way of communicating with coworkers located elsewhere in the plant. Because of the high noise levels, earphones must be worn to hear the radio communications. To be effective, the earphones must also block out some of the external noise. But if they block out too much of the external noise, the user will not be able to hear the conversations of nearby coworkers or the helpful sound queues of operating machinery. In airplanes, the airline pilot needs headphones that effectively block out the external engine noises. But the pilot also needs to hear the conversation of people who are nearby, such as their copilot or other airline support staff. In those applications, the around-the-ear headphones sometimes can cause unacceptable degradation of intelligibility of the conversations of such people.

The on-the-ear headphone, which is also referred to as the supra aural design, has an earphone cushion that simply rests against the ear when the headphone is being worn by the user. Typically, the cushion is made of an open cell foam material that easily transmits sound. This design tends to be lightweight, compact, and very comfortable. One disadvantage, however, is that conventional on-the-ear designs do not very effectively attenuate external noise. Thus, they are not well suited for use in noisy environments.

The in-the-ear headphone which typically provides less attenuation than the around-the-ear type has an ear piece that fits into the ear cavity, i.e., concha. Unlike the around-the-ear design, however, the in-the-ear headphone is typically very light and compact and thus for that reason it can be very comfortable to wear.

SUMMARY OF THE INVENTION

In general, in one aspect, the invention is an in-the-ear headphone including an earphone which is placed onto a user's ear. The earphone includes a shell body defining an internal cavity. The shell body has an extended portion shaped and sized to fit into a concha of the user's ear. The extended portion includes an aperture at an end thereof which aligns with the user's ear when the earphone is being worn by the user. The extended portion defines a passageway extending from the aperture to the internal cavity so that the internal cavity is acoustically coupled to the user's ear cavity when the headphone is being worn by the user. The earphone also includes a cushion covering at least part of the extended portion of the shell body and having an opening aligned with the aperture. The cushion may be made of a molded, self-skinned material.

Preferred embodiments include the following features. The cushion is made of a damped, compliant material and it includes bulbous portions near the opening and surrounding at least some of the aperture. The bulbous portions are in a range of about 3 to 5 millimeters in thickness. The internal cavity has a total volume that is larger than 10 cubic centimeters (e.g. 20 cc.). The aperture is oval-shaped and has dimensions of about 3 to 3.5 mm by about 8 to 10 mm. (i.e., it has an area that is between 25 to 35 $mm^2$). The earphone further includes an acoustic damping material within the internal cavity (e.g. an open cell foam).

In general, in another aspect, the invention is an in-the-ear headphone including an earphone which is placed onto a user's ear. The earphone includes a shell body defining an internal cavity. The shell body has an extended portion shaped and sized to fit into a concha of the user's ear. The extended portion includes an aperture at an end thereof which aligns with the user's ear when said earphone is being worn by the user and it defines a passageway extending from the aperture to the internal cavity so that the internal cavity is acoustically coupled to the user's ear cavity when the headphone is being worn by the user. The earphone also includes an acoustical driver mounted within the extended portion; and an acoustical microphone mounted within the extended portion. The microphone is located substantially between the driver and the aperture and near a lower edge of the aperture.

In preferred embodiments, the aperture is oval shaped and has a long axis and a short axis and the plane of the driver is substantially parallel to the long axis of the oval-shaped aperture. The aperture is oriented so that its long axis is oriented vertically when the earphone is worn by the user. Also, the plane of the driver and the plane of the aperture are oriented at an angle of between 45° and 90° with respect to each other. The earphone also includes a hollow tower structure within the shell body. The tower structure holds the driver within the earphone and defines a rear cavity behind the driver. The rear cavity is separate and substantially isolated from the internal cavity. The rear cavity has a volume that is substantially smaller than the volume of the internal cavity (e.g. 2 cubic centimeters). A wall of the rear cavity is formed by a section of the shell body and it includes a second aperture connecting the rear cavity to outside of the shell body. The said second aperture is covered by a material having an acoustic resistance. The tower structure includes a pressure equalization hole connecting the rear cavity to the internal cavity. The pressure equalization hole has a diameter of less than about 1 millimeter (e.g. 0.25 and 0.5 millimeters).

Also in preferred embodiments, the plane of the microphone is substantially perpendicular to the plane of the driver and the plane of the microphone forms an angle with the plane of the aperture of between 45° and 60°.

The in-the-ear headphone of the invention protects a user's ears by actively and passively attenuating external noise, which leaks into the users ear canal when the headphone is worn by the user, such that the total attenuation of the system is relatively flat across the audible frequencies. Total attenuation of better than about 15–25 dB is achievable with the invention. It has been shown that 20 db attenuation is sufficient for good hearing protection and yet it still enables people to hear each other when communicating in an industrial environment.

Other advantages and features will become apparent from the following description of the preferred embodiment and from the claims.

DESCRIPTION OF THE PREFERRED EMBODIMENTS

Figure 1:
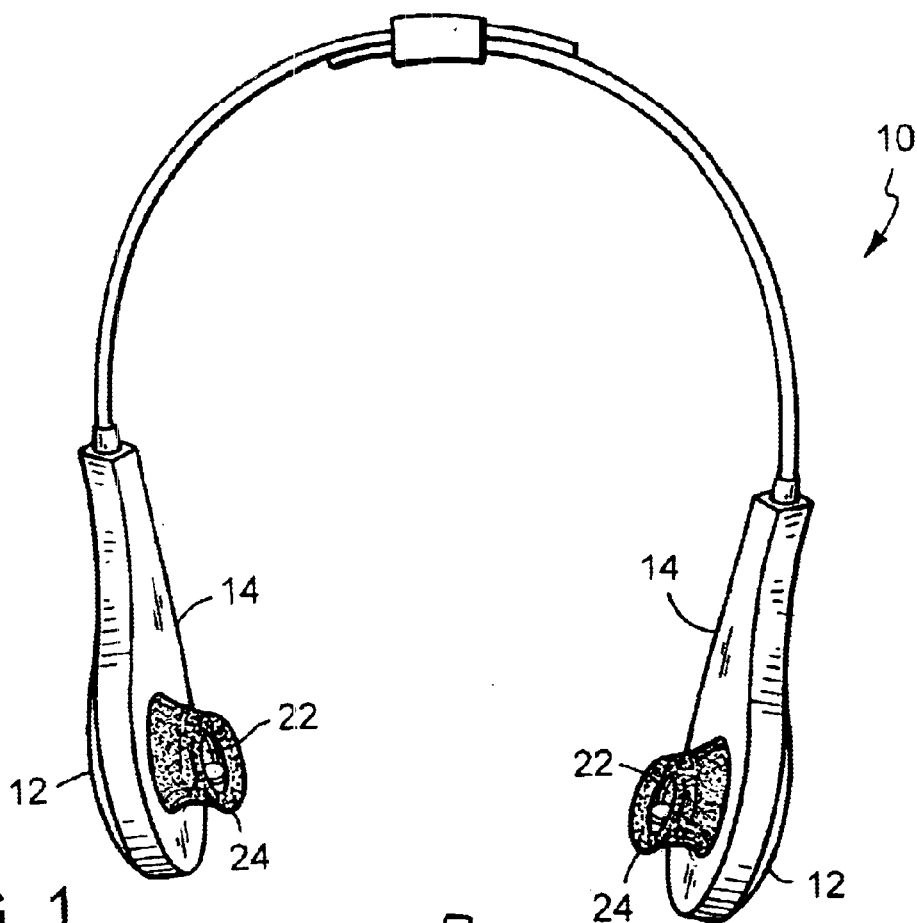
FIG. 1 shows a headphone with left and right in-the-ear earphones.
Figure 2:
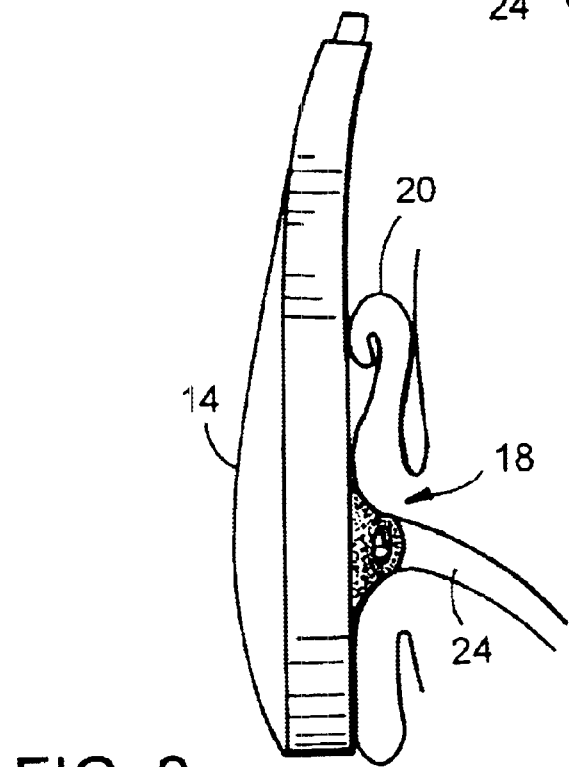
FIG. 2 is a side view of the in-the-ear earphone as it rests on a user's ear.

Referring to FIGS. 1, 2, 3, 4B and 5B, an in-the-ear headphone 10 has two earphones 12, one for the right ear and one for the left ear. Each earphone 12 includes a rigid shell 14 that defines an internal cavity 28 and that has an extended portion 16 which is sized and shaped to fit into the concha 18 of a user's ear 20. An oval-shaped aperture 22 at an end of the extended portion 16 aligns with the user's ear canal 24 to create an acoustical connection between the user's ear canal and internal cavity 28 when the headphone is worn by the user.

Typically, an adult user's ear cavity, i.e., the combined volume of the concha and the ear canal, is about two cubic centimeters (cc.) when the in-the-ear headphone is worn. Internal cavity 28 has a volume which is substantially larger than this. Theoretically, it can be shown that a volume that is about ten times the ear cavity volume will produce a passive attenuation of about 20 db. Thus, in the described embodiment, internal cavity has a volume of greater than about 20 cc. The invention, however, is not limited to using internal cavity sizes which are that large; noticeable passive attenuation will occur with smaller cavity sizes, e.g 10 cc.

A cushion 26 surrounds extended portion 16 of the shell and surrounds aperture 22 without obstructing it. In other words, cushion 26 includes an opening that aligns with and is approximately the same size as aperture 22. Cushion 26 is typically made of a molded, self skinned material that has a smooth surface which is capable of creating a good acoustical seal with user's ear. The material is also soft and highly compliant, such that it readily conforms to the human ear without having to apply much pressure. Additionally, the material is mechanically damped to give a low sound transmission capability. Typically, a heavily damped material also exhibits a slow recovery rate (e.g., on the order of seconds) to its original shape after being compressed. A suitable material which exhibits all of these properties is a urethane foam, such as is described in U.S. Pat. No. 4,158,087, or any other comparable material. Cushion 26 makes the headphones comfortable for the user to wear and, by forming a seal at the region of contact with the user's ear, reduces the amount of external ambient sound that is permitted to leak into the user's ear canal.

Figure 4B:
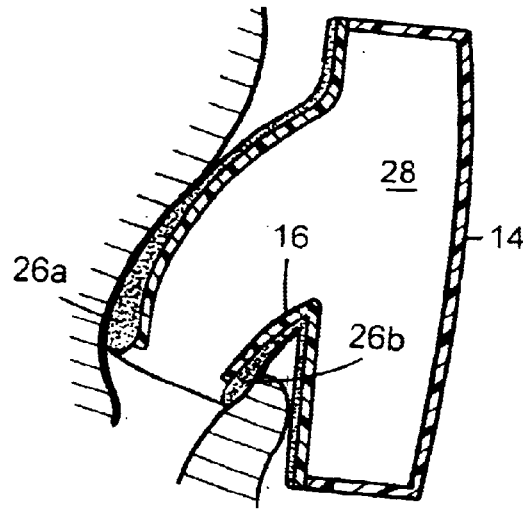
FIG. 4B is a cross-sectional view of the earphone cavity and cushion through section A—A in FIG. 3 and which also shows a top view of how the earphone fits within a person's ear.
Figure 4A:
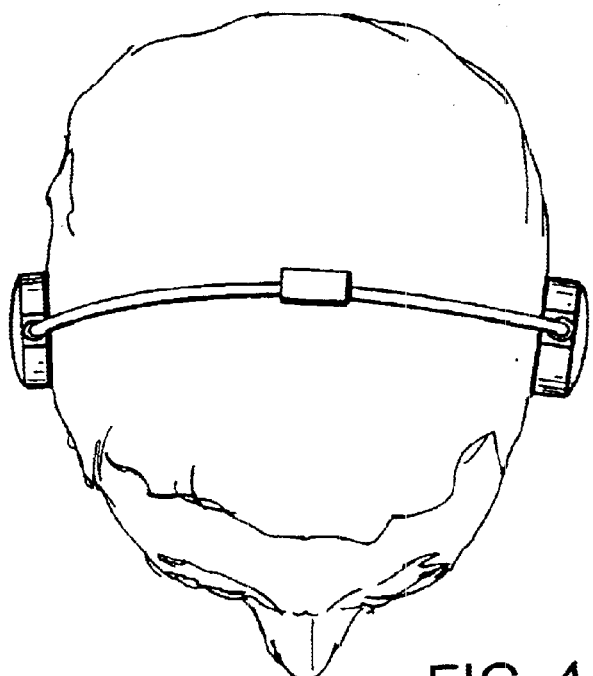
FIG. 4A is a top view of a person wearing the headphones shown in FIG. 1.
Figure 5B:
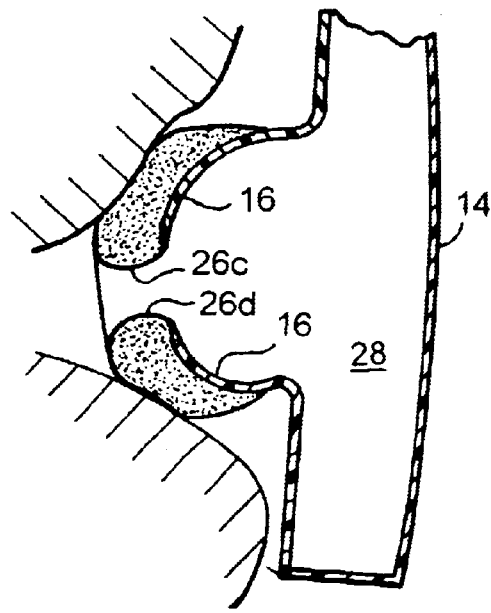
FIG. 5B is a cross-sectional view of the earphone through section B—B of FIG. 3 and which also shows a front view of how the earphone fits within a person's ear.

Referring to FIGS. 4B and 5B, in order to create an effective acoustical seal with a wide range of different ear shapes and sizes, cushion 26 has bulbous or expanded portions 26a, 26c, and 26d adjacent to the back, top, and bottom areas, respectively, of aperture 22. Bulbous portions 26a, 26c, and 26d of cushion 26 are thick enough to permit the cushion to compress and thereby conform to the different sizes and shapes of ear that might be encountered. In the described embodiment, bulbous portions 26a, 26c, and 26d are approximately three to five millimeters thick. The other regions of cushion including front portion 26b are much thinner, e.g. approximately one mm thick.

If extended portion 16 of shell 14 and cushion 26 are custom fitted to a particular user's ear, then cushion 26 can be made without bulbous portions 26a, 26c, and 26d. In other words, it can have substantially uniform thickness (e.g. 1 mm). Extended portion 16 can be custom molded to the shape of the concha of a user's ear by using a process similar to that used to custom mold hearing aids.

As best seen in FIGS. 4B and 5B, extended portion 16 is curved along substantially its entire length to substantially match the curvature of said concha and allow attachment around the extended portion of a cushion for establishing a seal between the extended portion and the user's ear.

Internal cavity 28 in combination with the user's ear cavity passively attenuates high frequency ambient noise. To improve the acoustic coupling between internal cavity 28 and the ear cavity and thereby improve attenuation efficiency of the earphone, aperture 22 is made as large as possible without compromising the cushion's ability to form a seal with the user's ear. Indeed, the larger one makes the size of aperture, the greater will be the bandwidth over which substantially the full level of passive attenuation will be achieved. The size of aperture 22 is limited, however, by the size of a typical user's ear. If aperture 22 is made too large, the cushion around aperture 22 will not make full contact with the user's ear at all locations surrounding the aperture. Thus, there will be portions through which external noise will be able to leak into the ear canal and degrade the low frequency attenuation performance of the earphone. In the described embodiment, aperture 22 has an oval shape with the dimension along its short axis being about 3–3.5 mm and the dimension along its long axis being by about 8–10 mm. In other words, aperture 22 has a total area of about 25–35 mm$^2$. An opening of this size extends the full achievable level of passive attenuation of the earphone down to a cutoff frequency of about 700–800 Hz, while still allowing the cushion to achieve a good seal with the wide variety of ear shapes and sizes that are likely to be encountered.

To improve the acoustic characteristics of the earphone, internal cavity 28 is filled with a sound absorbent material 30

(i.e., damping material), such as an open cell foam or fibrous material such as Thinsulate™ which is available from 3M (Minnesota, Mining and Manufacturing Corporation). Damping material 30 produces a more predictable, smoother transfer function and reduces cavity resonances.

Figures 6, 9:
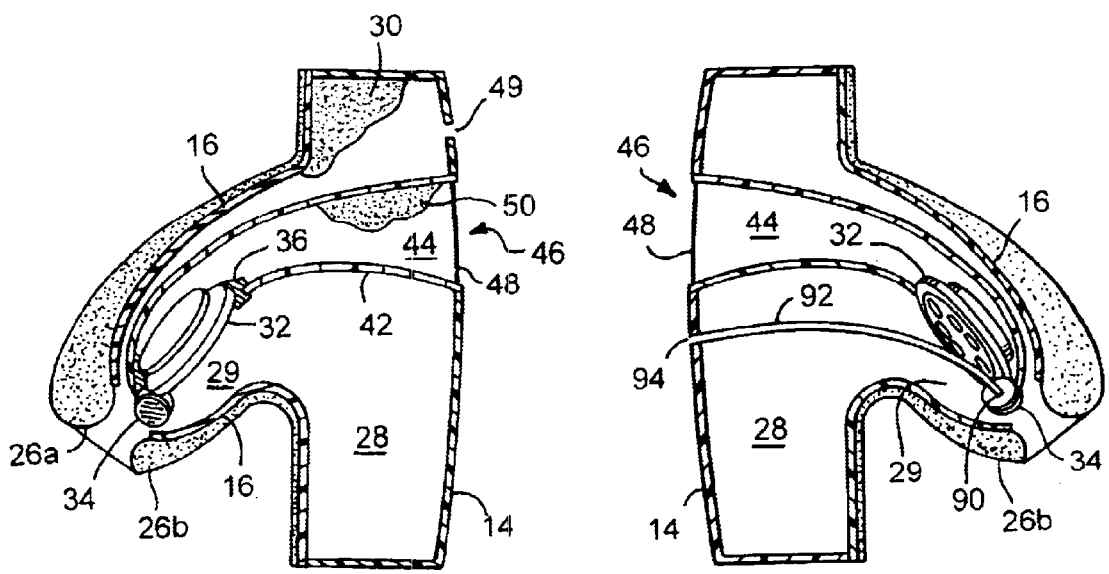
FIG. 6 shows a cross-sectional view of the earphone with driver and microphone through section A—A of FIG. 3.
FIG. 9 shows an alternative design for the driver/microphone combination.

Referring to FIG. 6, a driver 32 and a microphone 34 are mounted within internal cavity 28. As will be described below, they are used to actively attenuate higher frequency noise. Both driver 32 and microphone 34 are disk-shaped devices. Driver 32 is mounted inside of extended portion 16 of shell 14 and is oriented such that the plane of the disk-shaped driver is substantially parallel to the long axis of oval-shaped aperture 22 and forms an angle with the plane in which aperture 22 lies of between 45° to 90°, preferably closer to 90° (i.e., perpendicular). This particular orientation of driver 32 allows extended portion 16 of shell 14 to be made narrow enough so as to fit into a wide variety ear sizes. The orientation of driver 32 also is such as to present only minimal obstruction of a passageway 29 that extends through extended portion 16 and connects aperture 22 to the rest of internal cavity 28.

Figure 3:
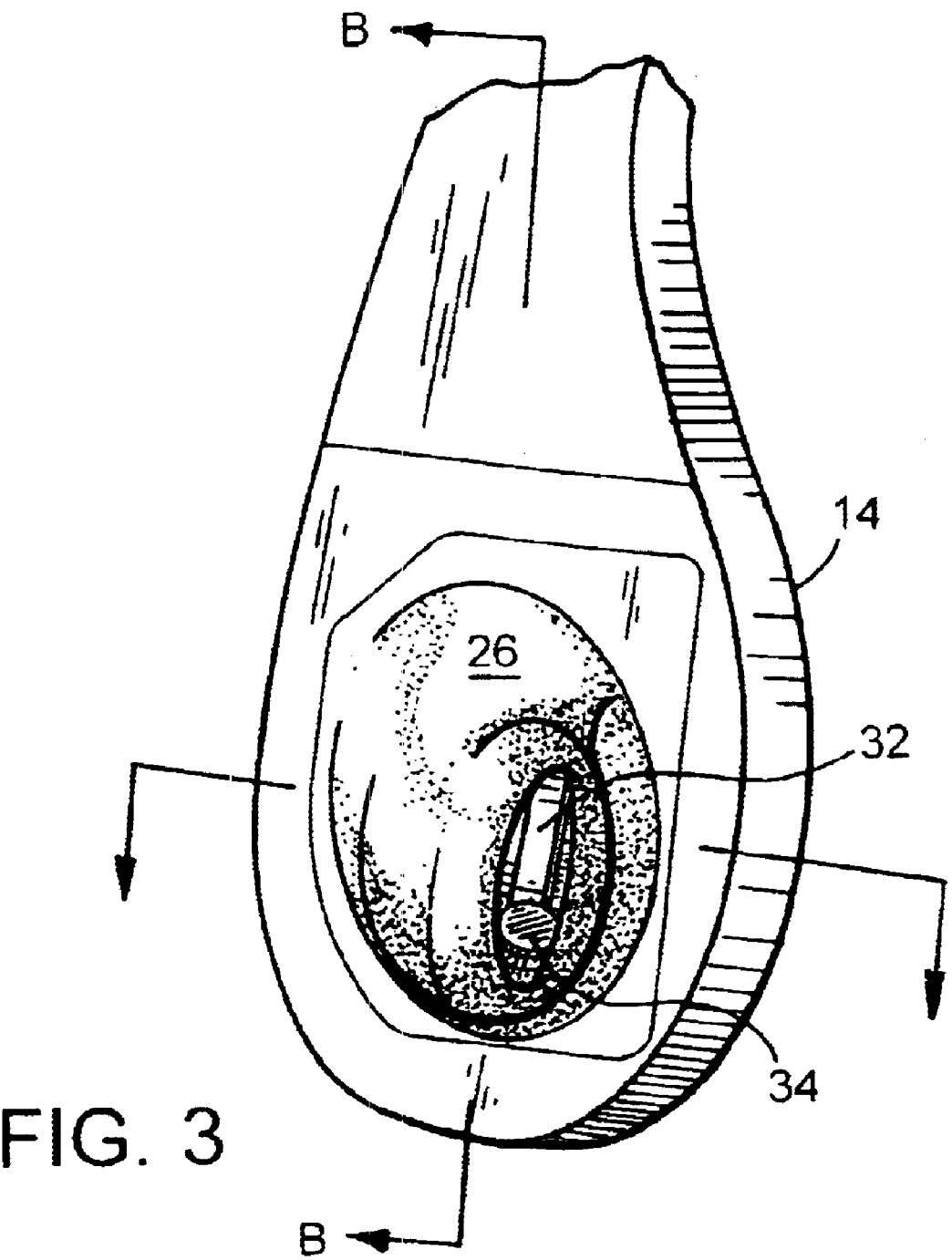
FIG. 3 shows the cushion side of the earphone.
Figure 5A:
FIG. 5A is a front view of the headphones as they are being worn by a person.

Microphone 34 is mounted on the edge of driver 32 and inside the extended portion 16, near aperture 22. More specifically, it is located near the lower side of aperture 22 and substantially between driver 32 and aperture 22. Microphone 34 is attached to the edge of driver 32 so that the plane in which it lies is substantially perpendicular to the plane in which driver 32 lies and angled slightly toward the plane of aperture 22 (e.g. forming an angle of between 45° and 60°). The front of microphone 34 faces upwards from the bottom of aperture 22 as indicated in FIGS. 3 and 6. In other words, microphone 34 is as close as possible to aperture 22, without obstructing aperture 22 and without extending out of aperture 22. Its location and orientation relative to driver 32 and aperture 22 produces minimum delay coupling between microphone 34 and driver 32 and particularly effective active noise cancellation in the region in which it is most desired, i.e., the user's ear cavity.

Driver 32 is a high compliance, high excursion driver which is between 15 to 20 mm in diameter. In the described embodiment, it is a Model TO16HO2 which is available from Foster of Japan. Microphone 34 is a much smaller diameter (e.g., six millimeter) device such as an EM 109 electric microphone available from Primo, Inc. of Japan (or an equivalent device).

Referring again to FIG. 6, both driver 32 and microphone 34 are mounted at one end of a hollow tower structure 42 within internal cavity 28. The opposite end of tower structure 42 is attached to a back wall of shell 14. Driver 32 is held within tower structure 42 by a flexible rubber or silicone grommet 36 which forms a seal between driver 32 and tower structure 42 around the perimeter of driver 32. Tower structure 42 defines a separate rear cavity 44 behind driver 32 that is smaller than and substantially isolated from internal cavity 28. In the described embodiment, rear cavity 44 has a volume of approximately two cubic centimeters and, like internal cavity 28, it is also filled with a damping material 50.

Grommet 36 is constructed so as to hold microphone 34 in position relative to driver 32. Due to the flexibility of the material of which grommet 36 is made, grommet 36 facilitates easy assembly of the earphone. Both driver 32 and microphone 34 can be easily slipped into their corresponding holes within grommet 36 and then grommet 36 can be easily inserted into the end of tower structure 42.

Shell 14 includes a circular opening 46 defining a passageway between rear cavity 44 and the outside. Opening 46 is covered with a resistive mesh 48. In the described embodiment, opening 46 has a diameter of approximately five mm and mesh 48 creates a resistance for opening 46 of approximately $1-2\times10^7$ acoustic ohms. The combination of the resistive mesh 48 and damping material 50 provides a controlled damping of driver 32 and it passively attenuates higher frequency noise which passes through driver 32 from the outside.

Shell 14 includes a pressure equalization hole 49, of about 0.25 to 0.5 millimeters in diameter, which enables pressure within the internal cavity 38 to equalize when the earphone is placed on the user's ear. In the described embodiment, equalization hole 49 passes through the backside of shell 14 so as to connect internal cavity 28 to the outside. Alternatively, pressure equalization hole 49 can be located in the wall of tower structure 42 thereby connecting internal cavity 28 with rear cavity 44. The acoustic resistance of this hole is about $1-2\times10^7$ acoustic ohms.

When a user is wearing the headphones, cushion 26 contacts the user's ear and forms a seal that tends to prevent air from entering or escaping from the enclosed region which is made up of the user's ear canal and internal cavity 28. Without a pressure equalization hole, movement of the headphones on the user's will tend to cause severe over pressure or under pressure conditions to occur within this enclosed region. This will typically make the earphones uncomfortable, may cause them to float or creep on the ear, and will tend degrade the acoustic seal between the cushion and the user's ear (and thereby degrade the passive attenuation). Pressure equalization hole 49, by allowing air to enter and leave internal cavity 28, prevents the over pressure and under pressure conditions from occurring.

Figure 7:
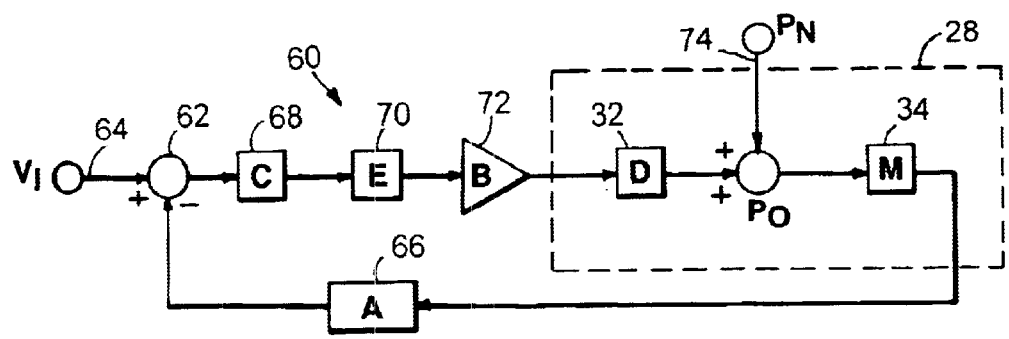
FIG. 7 is a block diagram of an active attenuation circuit.

An active attenuation circuit 60 of which driver 32 and microphone 34 form a part is shown in FIG. 7. Circuit 60 is duplicated for the other driver/microphone combination of the other earphone. Earphone 12 is represented by the dashed box and the driver and the microphone are identified, as before, by numbers 32 and 34, respectively. Driver 32 reproduces sound for a listener wearing the headphones and microphone 34 picks up this sound and low frequency ambient sound that is present in a cavity that exists between the earphone and the listener's ear. A preamplifier 66 amplifies the output signal from microphone 34 to produce a feedback signal that is fed back to a combiner circuit 62 at the input side of the circuit. Combiner circuit 62 adds the feedback signal to an input signal $V_I$, which represents the audio that is to be reproduced by the driver 32. The output of combiner circuit 62 passes first through a compressor circuit 68 which limits the amplitude of high level signals and then through a compensator circuit 70 which insures that the open-loop gain of the system meets the Nyquist stability criteria and thus does not oscillate.

The output of compensator circuit 70 passes to a power amplifier 72 and then to driver 32. Power amplifier 72 amplifies the signal to the level required for producing the desired sound level out of driver 32. The audio sound generated by driver 32 combines with ambient noise (identified as $P_N$ in FIG. 7) that leaks by the earphone cushion into the cavity formed between the earphone and the listener's ear. Thus, the signal that microphone 34 picks up represents the audio signal plus the ambient noise.

The active attenuation circuit attenuates noise over the low frequency range, e.g below 700–800 Hz. It is possible to increase the point at which the active attenuation rolls off, but this would be at the risk of making the system unstable. Noise at the higher frequencies is passively attenuated by the internal cavity coupled with the user's ear cavity. As noted previously, the low frequency cutoff of the passive attenuation is controlled in part by the size of aperture 22. If aperture 22 is made larger the effectiveness of the passive attenuation will extend to lower frequencies. With the aperture size used in the described embodiment (e.g. 25–35 mm$^2$), the passive attenuation extends down to about 700–800 Hz.

Figure 8:
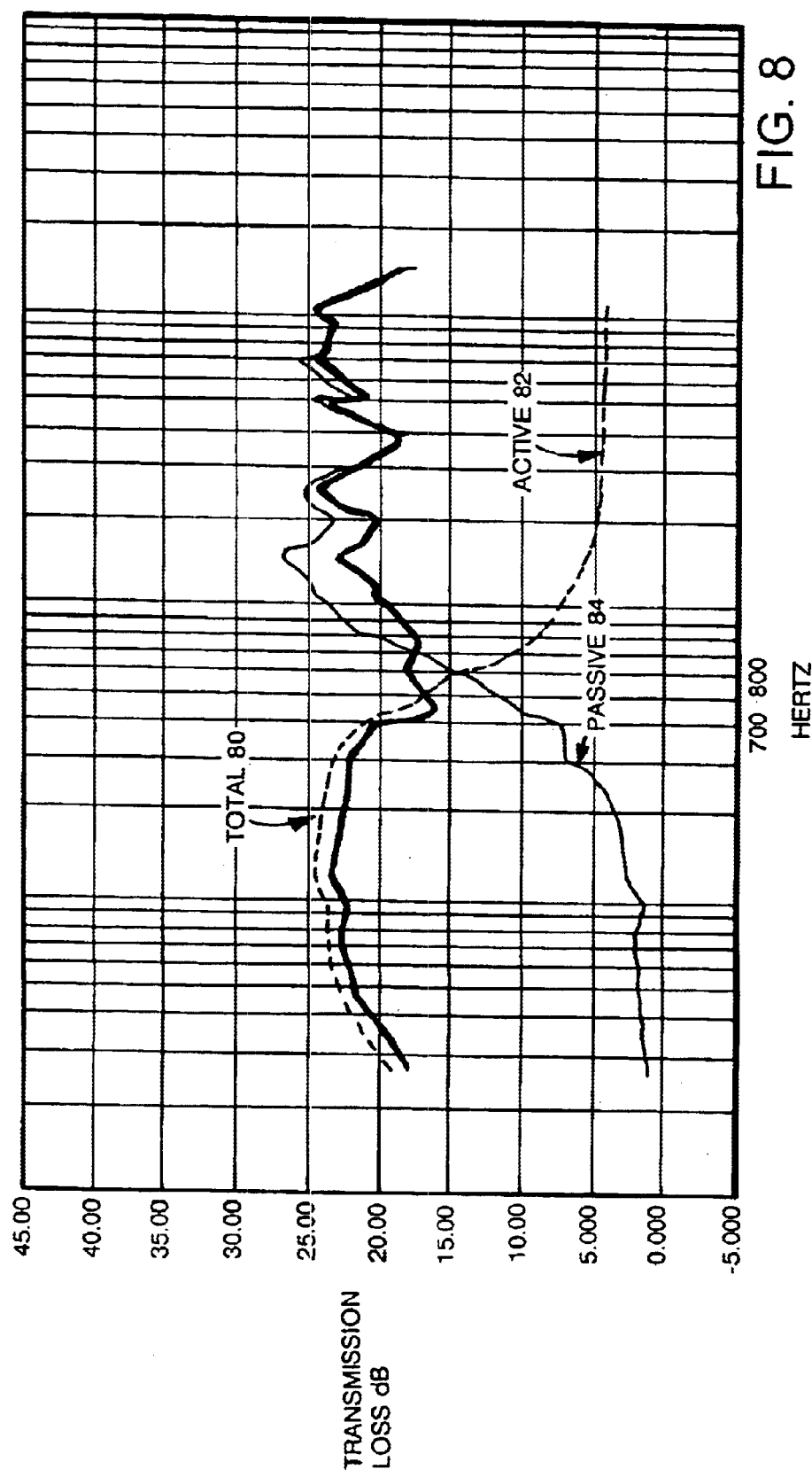
FIG. 8 illustrates the total attenuation provided by the invention.

Referring to FIG. 8, the total attenuation, line 80, provided by the headphones of the invention is a combination of active attenuation represented by curve 82 and passive attenuation represented by curve 84. The combination of active and passive attenuation provides a substantially flat attenuation of about 15–25 db across the audible frequencies.

Referring to FIG. 9, in an alternative embodiment, microphone 34 is modified by drilling a hole 90 in its back side. (Note that this drawing shows the microphone mounted in such a way that its back side is visible in the drawing; whereas FIG. 6 shows the microphone mounted so that its front side is visible.) The hole 90 is acoustically coupled to the outside of the shell (or alternatively to rear cavity 44) through conduit 92 and an equalization hole 94 in the wall of shell 14.

The advantage of this configuration, from a system stability point of view, is that the low frequency response of the microphone 34 becomes less of a factor, and from a control point of view, the clipping level of the system is increased at low frequencies. From an ambient noise point of view, the frequency response of the microphone will have first order roll-off (like a velocity microphone). By proper selection of the size of the equalization hole 90, it is possible to increase the maximum level of the ambient noise that the system can accept before clipping. Typically the pressure equalization hole should be chosen to provide roll-off at about thirty hertz without significantly affecting cancellation above one hundred hertz.

Other embodiments are within the following claims.

What is claimed is:

1. An in-the-ear earphone which is placed on a user's ear, said earphone comprising;
   a shell body defining an internal cavity, said shell body having an extended portion shaped and sized to fit into a concha of the user's ear, said extended portion including an aperture at an end thereof which aligns with the user's ear when said earphone is being worn by the user, said extended portion defining a passageway extending from said aperture to said internal cavity so that said internal cavity is acoustically coupled to the user B ear cavity when the headphone is being worn by the user,
   said extended portion being curved along substantially its entire length to substantially match the curvature of said concha and allow attachment around said extended portion of a cushion for establishing a seal between said extended portion and the user's ear.

2. The in-the-ear earphone according to claim 1 further comprising a cushion covering at least part of said extended portion of said shell body and having an opening aligned with said aperture.

3. The in-the-ear earphone according to claim 2, wherein said cushion is made of a molded, self-skinned material.

4. The in-the-ear earphone according to claim 2 wherein said cushion is made of a mechanically-damped compliant material.

5. The in-the-ear earphone according to claim 2 wherein said cushion includes a bulbous portion near the opening and surrounding at least some portions of said aperture.

6. The in-the-ear earphone according to claim 5 wherein said bulbous portion is in a range of about 3 to 5 millimeters in thickness.

7. The in-the-ear earphone according to claim 1, wherein said internal cavity is significantly larger than the ear canal of an average user.

8. The in-the-ear earphone according to claim 7 wherein said internal cavity has a total volume that is larger than 10 cubic centimeters.

9. The in-the-ear earphone according to claim 8 wherein said internal cavity has a total volume that is about 20 cubic centimeters.

10. The in-the-ear earphone according to claim 7 wherein said aperture is oval-shaped.

11. The in-the-ear earphone according to claim 10 wherein said aperture has dimensions of about 3 to 3.5 mm by about 8 to 10 mm.

12. The in-the-ear earphone according to claim 10 wherein said aperture has an area that is greater than about 25 square millimeters.

13. The in-the-ear earphone according to claim 12 wherein said aperture has an area that is in the range of about 25 to 35 square millimeters.

14. The in-the-ear earphone according to claim 7 wherein said extended portion is custom moldable to the concha of the user.

15. The in-the-ear earphone according to claim 7 wherein said earphone further comprises an acoustic damping material within said internal cavity.

16. The in-the-ear earphone according to claim 15 wherein said damping material is made of an open cell foam.

17. An in-the-ear earphone which is placed on a user's ear, said earphone comprising:
   a shell body defining an internal cavity, said shell body having an extended portion shaped and sized to fit into a concha of the user's ear, said extended portion including an aperture at an end thereof which aligns with the user's ear when said earphone is being worn by the user, said extended portion defining a passageway extending from said aperture to said internal cavity so that said internal cavity is acoustically coupled to the user's ear cavity when the earphone is being worn by the user;
   an acoustical driver mounted within said extended portion; and
   an acoustical microphone mounted within said extended portion, said microphone located substantially between said driver and said aperture and near a lower edge of said aperture;
   said extended portion being curved along substantially its entire length to substantially match the curvature of said concha and allow attachment around said extended portion of a cushion for establishing a seal between said extended portion and the user's ear.

18. The in-the-ear earphone of claim 17 wherein said aperture is oval shaped and has a long axis and a short axis, wherein said driver lies in a first plane, and wherein said first plane is substantially parallel to the long axis of said oval-shaped aperture.

19. The in-the-ear earphone of claim 17 wherein said aperture lies substantially within a second plane and where said first plane and said second plane are oriented at an angle of between 45° and 90° with respect to each other.

20. The in-the-ear earphone of claim 17 wherein the earphone further comprises a hollow tower structure within said shell body, said tower structure holding said driver within said earphone and defining a rear cavity behind said driver, said rear cavity separate from said internal cavity.

21. The in-the-ear earphone according to claim 20 wherein said rear cavity is substantially isolated from said internal cavity.

22. The in-the-ear earphone according to claim 21 wherein said rear cavity has a volume that is substantially smaller than the volume of the internal cavity.

23. The in-the-ear earphone according to claim 20 wherein a wall of said rear cavity is formed by a section of said shell body and wherein said section of said shell includes a second aperture connecting said rear cavity to outside of said shell body.

24. The in-the-ear earphone according to claim 23 wherein said second aperture is covered by a mesh having an acoustic resistance.

25. The in-the-ear earphone according to claim 24 wherein said rear cavity has a volume that is substantially smaller than the volume of the internal cavity.

26. The in-the-ear earphone according to claim 24 further comprising an acoustic damping material within said rear cavity.

27. The in-the-ear earphone according to claim 26 wherein said damping material is an open cell foam.

28. The in-the-ear earphone according to claim 20 wherein said tower structure includes a pressure equalization hole connecting the rear cavity to the internal cavity.

29. The in-the-ear earphone according to claim 28 wherein the pressure equalization hole has a diameter of less than about 1 millimeter.

30. The in-the-ear earphone according to claim 20 wherein said internal cavity has a total volume that is larger than 10 cubic centimeters.

31. The in-the-ear earphone according to claim 30 further comprising an acoustic damping material within said internal cavity.

32. The in-the-ear earphone according to claim 31 wherein said damping material is made of an open cell foam.

33. The in-the-ear earphone according to claim 20 wherein said aperture is oval-shaped.

34. The in-the-ear earphone according to claim 33 wherein said aperture has dimensions of about 3 to 3.5 mm by about 8 to 10 mm.

35. The in-the-ear earphone according to claim 34 wherein said aperture has an area that is greater than about 25 millimeters.

36. The in-the-ear earphone according to claim 35 wherein said aperture has an area that is in the range of about 25 to 35 square millimeters.

37. The in-the-ear earphone according to claim 17 wherein said shell body includes a pressure equalization hole connecting said internal cavity to outside of said shell body.

38. The in-the-ear earphone according to claim 37 wherein the pressure equalization hole has a diameter of less than about 1 millimeter.

39. The in-the-ear earphone according to claim 17 further comprising:
   cushion covering at least part of said extended portion of said shell body and having an opening aligned with said aperture, wherein said cushion is made of a molded, self-skinned material.

40. The in-the-ear earphone according to claim 39 wherein said cushion is made of a mechanically damped, compliant material.

41. The in-the-ear earphone according to claim 39 wherein said cushion includes a bulbous portion near the opening and surrounding at least some of said aperture.

42. The in-the-ear earphone according to claim 41 wherein said bulbous portion is in a range of about 3 to 5 millimeters in thickness.

43. The in-the-ear earphone of claim 17 wherein said driver lies in a first plane and said microphone lies in a second plane and wherein said second plane is substantially perpendicular to said first plane.

44. The in-the-ear earphone of claim 17 wherein said driver lies in a first plane, said microphone lies in a second plane and said aperture lies in a third plane and wherein said second plane forms an angle with said third plane of between 45° and 60°.

45. The in-the-ear earphone of claim 44 wherein said second plane is substantially perpendicular to said first plane.

* * * * *